United States Patent
Poland

(10) Patent No.: US 11,992,371 B2
(45) Date of Patent: May 28, 2024

(54) MULTI-PURPOSE ULTRASOUND IMAGE ACQUISITION DEVICE

(71) Applicant: KONINKLIJKE PHILIPS N.V., Eindhoven (NL)

(72) Inventor: McKee Poland, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 760 days.

(21) Appl. No.: 16/132,836

(22) Filed: Sep. 17, 2018

(65) Prior Publication Data

US 2019/0015079 A1 Jan. 17, 2019

Related U.S. Application Data

(63) Continuation of application No. 14/772,111, filed as application No. PCT/IB2014/059380 on Mar. 3, 2014, now Pat. No. 10,085,723.

(60) Provisional application No. 61/774,196, filed on Mar. 7, 2013.

(51) Int. Cl.
*A61B 8/00* (2006.01)
*A61B 8/08* (2006.01)
*A61B 8/14* (2006.01)

(52) U.S. Cl.
CPC .............. *A61B 8/56* (2013.01); *A61B 8/145* (2013.01); *A61B 8/4405* (2013.01); *A61B 8/4411* (2013.01); *A61B 8/4427* (2013.01); *A61B 8/4433* (2013.01); *A61B 8/4444* (2013.01); *A61B 8/4483* (2013.01); *A61B 8/462* (2013.01); *A61B 8/464* (2013.01); *A61B 8/466* (2013.01); *A61B 8/467* (2013.01); *A61B 8/483* (2013.01); *A61B 8/5207* (2013.01); *A61B 8/54* (2013.01)

(58) Field of Classification Search
None
See application file for complete search history.

(56) References Cited

U.S. PATENT DOCUMENTS

| | | | |
|---|---|---|---|
| 6,279,399 B1 | 8/2001 | Holm | |
| 6,440,072 B1* | 8/2002 | Schuman | A61B 5/0017 600/437 |
| 6,475,146 B1* | 11/2002 | Frelburger | A61B 5/0002 600/437 |
| 6,540,682 B1 | 4/2003 | Leavitt et al. | |
| 7,141,020 B2 | 11/2006 | Poland | |

(Continued)

FOREIGN PATENT DOCUMENTS

| | | |
|---|---|---|
| JP | 2010227357 A | 10/2010 |
| WO | 2006111872 A2 | 10/2006 |

(Continued)

*Primary Examiner* — Katherine L Fernandez
*Assistant Examiner* — Farouk A Bruce

(57) ABSTRACT

The present invention relates to an ultrasound image acquisition device (46) for use together with a console device (16, 18) to form an ultrasound imaging system (10) and a corresponding method. The ultrasound image acquisition device (46) particularly comprises a recognition device for recognizing an operating mode of the ultrasound image acquisition device, wherein the recognition device is configured to recognize the operating mode depending on a type of the console device (16, 18) and/or an applicable communication standard of the interface (50). By this, a dual purpose image acquisition probe (14) may be provided.

8 Claims, 9 Drawing Sheets

(56) References Cited

U.S. PATENT DOCUMENTS

| | | |
|---|---|---|
| 2002/0035328 A1 | 3/2002 | Roundhill et al. |
| 2002/0122056 A1* | 9/2002 | Bhesania ................ G06F 9/451 |
| | | 715/744 |
| 2003/0158482 A1* | 8/2003 | Poland ................ G01S 7/52079 |
| | | 600/446 |
| 2004/0123106 A1* | 6/2004 | D'Angelo ................ G06F 21/32 |
| | | 713/171 |
| 2005/0251035 A1 | 11/2005 | Wong |
| 2006/0058652 A1* | 3/2006 | Little ........................ A61B 8/56 |
| | | 600/437 |
| 2006/0161701 A1* | 7/2006 | Park ...................... G06F 13/102 |
| | | 710/63 |
| 2007/0167812 A1* | 7/2007 | Lemmerhirt .......... B06B 1/0292 |
| | | 600/459 |
| 2008/0112265 A1 | 5/2008 | Urbano |
| 2008/0146922 A1* | 6/2008 | Steins ................... G06F 1/1616 |
| | | 600/437 |
| 2008/0255451 A1 | 10/2008 | Cohen |
| 2010/0010508 A1 | 1/2010 | Takahashi et al. |
| 2010/0160785 A1* | 6/2010 | Poland .................. G01S 7/5208 |
| | | 600/459 |
| 2010/0249600 A1 | 9/2010 | Kudoh et al. |
| 2010/0305444 A1 | 12/2010 | Fujii |
| 2011/0077515 A1 | 3/2011 | Gerard et al. |
| 2012/0022379 A1* | 1/2012 | Gubbini ................. A61B 8/467 |
| | | 600/461 |
| 2012/0099773 A1* | 4/2012 | Halmann ............ G01S 7/52046 |
| | | 600/440 |
| 2013/0054467 A1* | 2/2013 | Dala .................... G06F 21/6245 |
| | | 705/51 |

FOREIGN PATENT DOCUMENTS

| | | | |
|---|---|---|---|
| WO | 2006111873 A2 | 10/2006 | |
| WO | WO-2009077983 A1 * | 6/2009 | ............... A61B 8/00 |
| WO | WO-2009105961 A1 * | 9/2009 | ............... A61B 8/00 |

\* cited by examiner

MULTI-PURPOSE ULTRASOUND IMAGE ACQUISITION DEVICE

The present application is a continuation of U.S. patent application Ser. No. 14/772,111 filed Sep. 2, 2015, which is the U.S. National Phase application under 35 U.S.C. § 371 of International Application No. PCT/IB2014/059380, filed Mar. 3, 2014, which claims the benefit of U.S. Provisional Application Ser. No. 61/774,196 filed Mar. 7, 2013. These applications are hereby incorporated by reference herein.

FIELD OF THE INVENTION

The present invention relates to an ultrasound image acquisition device for use together with a console device to form an ultrasound imaging system. Further, the present invention relates to an ultrasound imaging system for providing an image of an anatomical site, for example an anatomical view within a body of a patient.

BACKGROUND OF THE INVENTION

Ultrasound imaging systems are widely known in the art. They are in particular used to provide anatomical imaging of views within the body of patients. Both two-dimensional and three-dimensional imaging of bodies of patients is known to provide a reliable tool for medical practitioners to view parts of a body of a patient without the need for any surgical steps.

In three-dimensional ultrasound imaging, or volume imaging, the acquisition of a three-dimensional image may be accomplished by conducting many two-dimensional scans that slice through the volume of interest. Hence, a multitude of two-dimensional images that lie next to another is acquired. By proper image processing, a three-dimensional image of the volume of interest can be built out of the multitude of two-dimensional images. The three-dimensional information acquired from the multitude of two-dimensional images is displayed in proper form on a display for the user of the ultrasound system.

Further, so-called live three-dimensional imaging, or 4D imaging, is often used in clinical applications. In live three-dimensional imaging, a real-time view on the volume can be acquired enabling a user to view moving parts of the anatomical site, for example a beating heart or other organs.

Ultrasound imaging systems are typically complete stations that may be fixed to a certain location and are often movable on rollers to provide flexible use in different locations. The ultrasound imaging systems provide for every component needed to acquire ultrasound images, i.e. input devices, display devices, any computer hardware needed to run the ultrasound imaging system and the specific software for acquiring, rendering and displaying the ultrasound images. Further, the ultrasound imaging systems comprise at least one probe carrying one- or two-dimensional transducer arrays to scan the body of a patient either manually or automatically. In order to provide three-dimensional imaging, a probe may utilize a two-dimensional transducer array to electronically steer scan lines in a three-dimensional space. Alternatively, using a one-dimensional transducer array, the array may be scanned manually or automatically by means of a motor to steer scan lines in three-dimensional space.

Of course, providing fully set up ultrasound imaging systems comprising every component as mentioned above makes these systems not only relatively costly but also large, heavy and inconvenient to move in medical locations.

Further, mobile computational devices are commonly known and have spread throughout clinical applications in the last couple of years. Nowadays, mobile phones, tablets, personal computers and notebooks are largely used to provide all kinds of applications and network access independent of their location. These mobile consoles have steadily increasing hardware performance levels, easy to use interfaces and displays with increasing resolution and quality. However, battery power and battery life may be a constraint to such devices.

Recent developments have enhanced the functionality of such mobile devices.

Document WO 2006/11873 A2 discloses an ultrasonic diagnostic imaging system including analog and/or digital components which are configurable by firmware data. An ultrasound probe contains firmware data for configuring the programmable devices of an ultrasound system for operation with the probe. The firmware data is uploaded from the probe and used to configure the analog and/or digital components for operation with the probe at runtime.

There is a need to further improve ultrasound imaging systems in terms of costs, portability and multipurpose functionality.

SUMMARY OF THE INVENTION

It is an object of the present invention to provide an improved ultrasound image acquisition device and an improved ultrasound imaging system.

In a first aspect of the present invention an ultrasound image acquisition device for use together with a console device to form an ultrasound imaging system is presented that comprises a transducer array configured to provide an ultrasound receive signal, an image acquisition hardware assembly having a beam former configured to control the transducer array, and further configured to receive the ultrasound receive signal and to provide an image signal, and a signal processor configured to receive the image signal and to provide image data, an interface for connecting the ultrasound image acquisition device with a console device, and a recognition device for recognizing an operating mode of the ultrasound image acquisition device, wherein the recognition device is configured to recognize the operating mode depending on a type of the console device and/or an applicable communication standard of the interface.

In a further aspect of the present invention an ultrasound imaging system for providing an ultrasound image is presented that comprises the ultrasound image acquisition device comprising a transducer array configured to provide an ultrasound receive signal, an image acquisition hardware assembly having a beam former configured to control the transducer array, and further configured to receive the ultrasound receive signal and to provide an image signal, and a signal processor configured to receive the image signal and to provide image data, an interface for connecting the ultrasound image acquisition device with a console device, and a recognition device for recognizing an operating mode of the ultrasound image acquisition device, wherein the recognition device is configured to recognize the operating mode depending on a type of the console device and/or an applicable communication standard of the interface, and a console device, wherein the console device has a display and an input device, and wherein the console device and the ultrasound image acquisition device are connected via the interface.

In a further aspect of the present invention an ultrasound image acquisition kit for providing an ultrasound image, comprising an ultrasound image acquisition device comprising a transducer array configured to provide an ultrasound receive signal, an image acquisition hardware assembly having a beam former configured to control the transducer array, and further configured to receive the ultrasound receive signal and to provide an image signal, and a signal processor configured to receive the image signal and to provide image data, an interface for connecting the ultrasound image acquisition device with a console device, and a recognition device for recognizing an operating mode of the ultrasound image acquisition device, wherein the recognition device is configured to recognize the operating mode depending on a type of the console device and/or an applicable communication standard of the interface, and at least two console devices, wherein one of the console devices is a mobile console and another of the console devices is a cart-supported console, and wherein the ultrasound image acquisition device is connectable to one of the console devices via the interface.

In a further aspect of the present invention a method for specifying an operating state for an ultrasound image acquisition is provided that comprises the steps of providing an ultrasound image acquisition device comprising a transducer array configured to provide an ultrasound receive signal, an image acquisition hardware assembly having a beam former configured to control the transducer array, and further configured to receive the ultrasound receive signal and to provide an image signal, and a signal processor configured to receive the image signal and to provide image data, an interface for connecting the ultrasound image acquisition device with a console device, and a recognition device for recognizing an operating mode of the ultrasound image acquisition device, wherein the recognition device is configured to recognize the operating mode depending on a type of the console device and/or an applicable communication standard of the interface; connecting the ultrasound image acquisition device to a console device; recognizing an operating mode depending on a type of the console device via the recognition device of the ultrasound image acquisition device; and switching the transducer array and/or the image acquisition hardware assembly between at least two operating states based on the recognized operating mode.

It is a basic idea of the current invention to provide an ultrasound probe that has at least two purposes, namely a high performance two-dimensional or three-dimensional imaging when it is connected to a high performance and, preferably, cart-supported host system that contains powerful CPU and graphics equipment and, further, a lower performance two-dimensional or multi-plane imaging when the probe is connected to a commercial off the shelf (COTS) portable mobile device, for example a tablet, with less powerful CPU and graphics equipment. For example, the interface can be embedded with the USB (Universal Serial Bus) 3.0 standard, since it switches automatically to the lower power and speed of the USB 2.0 operating mode when equipped to a corresponding interface of a console device. Furthermore, a proposed probe may rely on encapsulating all ultrasound acquisition hardware into the probe itself, so that it can adapt to the processing and graphics capabilities of the host. The cost of ownership may be reduced by carrying a single probe for use with either host. Further, such mobile ultrasound image acquisition equipment makes the use of ultrasound imaging in clinical environments more convenient.

As the image acquisition device, for example the portable probe, is able to automatically adapt to the processing and graphics capabilities of the host, it may also be named "smart probe".

The costs of ownership are further reduced. A clinician possesses and carries merely one probe for use on systems with varying form factors and performance levels. For an advanced exam, the clinician may plug the probe into a cart-based system and is able to access high performance imaging, two-dimensional planar and three-dimensional volume rendering. For mobile, fast exams, the clinician may plug the same probe into a tablet or a patient monitor, such as the Philips MX 800 with an embedded personal computer, or a COTS handheld device. None of the host systems must contain ultrasound acquisition hardware, since it may be provided in the probe. Typically, larger cart-supported systems as console devices are likely to include further ultrasound acquisition hardware, as they are also compatible with non-smart (passive) probes. Small hosts like mobile devices certainly do not have their own acquisition hardware and are accordingly small and cheap. Hence, such mobile devices may provide simple two-dimensional and multi-plane imaging, at lower frame rates, with less post-processing and with simple applications. Moreover, the mobile configuration may also lower power consumption and dissipation of the probe, because it consumes less power when scanning in fewer dimensions, at lower frame rates, and with less acquisition signal processing according to the simpler, lower performance image displays.

Preferred embodiments of the invention are defined in the dependent claims. It shall be understood that the claimed method has similar and/or identical preferred embodiments as the claimed device and as defined in the dependent claims.

In an embodiment, the image acquisition device is configured to switch the transducer array and/or the image acquisition hardware assembly between at least two operating states based on the recognized operating mode. Hence, the transducer array and/or the image acquisition hardware assembly may be operated in two different states, one for high performance ultrasound imaging, in particular three-dimensional volume rendering, and a second for low performance ultrasound imaging, for example mere two-dimensional planar imaging. By this, one connected to a mobile console, for example, the ultrasound image acquisition device may be switched into a state that consumes less power.

In a further embodiment, the image acquisition device is configured to switch the transducer array and/or the image acquisition hardware assembly between at least a first operating state and a second operating state, wherein in the first operating state the transducer array and/or the image acquisition hardware assembly consume more power than in the second operating state. By this, significant power can be saved when connected to a mobile device. In this case, the whole ultrasound image acquisition device may be battery-powered by the battery of a mobile console.

In a further embodiment, the interface is configured to support at least two communication standards. By this, a recognition of an operating mode may also be recognized by an applicable communication standard. For example, if the interface is able to operate in an USB 3.0 and an USB 2.0 standard, a protocol of the communication standard may be used to identify the type of console device the ultrasound image acquisition device is attached to. In case only the establishment of a USB 2.0 standard should be possible for the communication via the interface, it could be concluded that only a mobile device is connected. Further, for example, in case an USB 3.0 standard could be established for the communication via the interface, it could be concluded that due to the high transfer rate a high performance ultrasound imaging is possible. Further, since the USB 3.0 standard provides more power at its interface port than USB 2.0, the power consumption of the image acquisition device may be increased accordingly when connected to the USB 3.0 interface, allowing higher frame rate scanning and more signal acquisition processing.

In a further embodiment, the image acquisition device is configured to switch the interface into a first communication standard in the first operating mode and into a second communication standard in the second operating mode, wherein the first communication standard has a higher data transfer rate than the second communication standard. By this, as previously explained, a recognition of the operating state may also be accomplished by identifying the possible communication protocol between the console device and the image acquisition device.

In a further embodiment, a first recognizable type of the console device is a mobile console and a second recognizable type of the console device is a cart-supported console. Hence, the ultrasound image acquisition device may be configured to recognize a type of console device attached to it. This may be conducted by reading out any type of identification element or recognition partner element within the console device via the recognition device of the image acquisition device. A "mobile console" may also be understood as a portable console. A "cart-supported console" may also be understood as a non-portable console.

In a further embodiment, the first operating state enables a two-dimensional planar ultrasound image acquisition and the second operating state enables a three-dimensional volume ultrasound image acquisition. By this, as previously explained, it will be possible to switch the ultrasound image acquisition device selectively into a state with less power consumption.

In a further embodiment, the ultrasound acquisition device is a portable probe having a probe housing, and wherein the transducer array and the image acquisition hardware assembly are located within the probe housing. By this, the so-called "smart probe" can be provided. All ultrasound-specific hardware components are located within the probe housing. Further, there is only needed a commercial off the shelf device as a mobile console to complete a fully functioning ultrasound imaging system.

The total power consumption of the probe may be less than 5 W. A probe weight may be less than 200 g. Hence, a flexible system with a mere need to connect the ultrasound acquisition device embodied as a probe to the console device can be provided. By providing all ultrasound image acquisition hardware in the probe, the bandwidth of the interface needs only to be sufficient to transmit image data and display data to the console device. Hence, not only single images may be transmitted for storing or display on the console device, but also live-streaming of the image data and/or display data to the console device may be enabled. Display data may comprise textural information, such as the user selected gain level, or graphical data, such as status icons.

In a further embodiment, the ultrasound image acquisition device further comprises an image processor configured to receive the image data and to provide display data. By this, image processing can also be provided within the ultrasound image acquisition device and there is no need in the console device to provide for such processing equipment.

In a further embodiment, the ultrasound image acquisition device comprises a master beam former and a multitude of micro-beam formers. By this, a possibility of a micro-beam forming and cascaded beam forming is provided. Further, the number of conductors needed to be provided via the interface can be reduced.

The interface might have, for example, four conductors in USB versus more than a hundred conductors for legacy passive probes. The reduction is generally due to the presence of the entire ultrasound acquisition hardware in the probe, including the, in particular cascaded, beamforming, the amplification, digitization, filtering, analytic detection, logging, and optionally scan conversion stages. These stages are referred to herein as beamforming, signal processing, and image processing. The result of those processes greatly reduces the bandwidth of the data, to the level at which transmission over an interface like USB is possible. In general, ultrasound acquisition processing yields a tremendous compression of the raw data: for example, individual data streams from hundreds (2D array) or thousands (matrix array) of elements on the sensor, each running at approximately 200 MBits/sec, are beamformed and detected into a single data stream less than, typically 50 Mbits/sec. It is the latter data stream that is sent over the USB interface. Hence, in particular both beamforming and signal processing, but not necessarily image processing, are required within in the probe in order to significantly reduce the number of conductors in the interface.

In a further embodiment, the interface is a cable-connect interface, wherein the interface further has a power line powering the ultrasound image acquisition device. By this, the ultrasound image acquisition device does not need any further external power connection. The ultrasound image acquisition device is port-powered via the already provided interface. Of course, the ultrasound image acquisition device may also be powered by battery.

In a further embodiment of the ultrasound imaging system, the console device is a mobile console comprising a central processing unit for operating the mobile console and a display unit configured to receive the display data and to provide the image. By this, mobile consoles may be used together with the ultrasound image acquisition device to form the ultrasound imaging system.

In a further embodiment, the console device is a cart-supported console. Further, the cart-supported console may comprise a further image acquisition and processing hardware assembly, wherein the further image acquisition and processing hardware assembly comprises at least one of a group consisting of a beam former configured to control the transducer array, and further configured to receive the ultrasound receive signal and to provide an image signal, a signal processor configured to receive the image signal and to provide image data, and an image processor configured to receive the image data from the signal processor and provide display data. By this, the image acquisition device may also be connected to a non-portable host to make use of the additional image acquisition and processing hardware assembly to provide high- and ultrasound-image acquisition, for example three-dimensional and 4D live ultrasound image acquisition.

An advantage of the acquisition hardware being present in the non-portable or cart-supported console is to allow the connection of legacy passive transducer probes, or probes with less acquisition hardware than the smart probe. As such, the non-portable host is compatible with the smart probe but may also be compatible with older, less integrated probes. The additional image processing circuitry of the non-portable host may be used with the smart probe to process and render higher quality and 3D images. The acquisition hardware in the non-portable host, for example, may not be used with the smart probe in an embodiment.

As already laid out above, in an embodiment, the interface is a cable connected interface. By this, the recognition device may easily detect a type of the console device and/or a communication standard of the interface.

In a further embodiment, the ultrasound image acquisition device further comprises an input device for enabling a user to command the ultrasound imaging system. By this, providing an input to the ultrasound imaging system is facilitated as the user may do so readily with the ultrasound image acquisition device. For example, if the ultrasound image acquisition device is a smart probe, it may include a button on the probe housing that allows the user to switch imaging modes or start and stop scanning.

In a further embodiment, the ultrasound image acquisition device has an intermediate connection device, wherein the transducer array is located within the probe, wherein the probe and the intermediate connection device are connected via an intermediate interface, and wherein the intermediate interface is a cable connected intermediate interface. By this, an embodiment may be provided where the image acquisition hardware assembly is located in the intermediate connection device that may be formed as an intermediate box that contains all acquisition hardware. An intermediate connection device may in turn connect to the console device, by means of the afore-mentioned interface. By this, the probe may be designed with less weight and, for example, the intermediate connection device may be positioned at a specific location that provides for good connection capabilities like good wireless capabilities or an easy to access cable connection port for the console device and the ultrasound image acquisition device.

In a further embodiment, the console device has a memory unit having stored thereon an application for viewing the display data on the display of the console device. By this, any commercial off the shelf device may be used as a mobile console.

In a further embodiment, the console device is a mobile console which is a personal digital assistant or a smartphone or a tablet-type personal computer or a clamshell-type personal computer or a convertible-type personal computer or a hybrid-type personal computer. These various types of personal computers are readily available commercially and hence may serve as a mobile console for the current invention.

In particular, the interface may use an USB 3.0 or USB 2.0 communication standard. In particular, the interface may be a wired interface with a cable comprising ten or fewer conductors. Further, the interface may be a Thunderbolt® interface.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
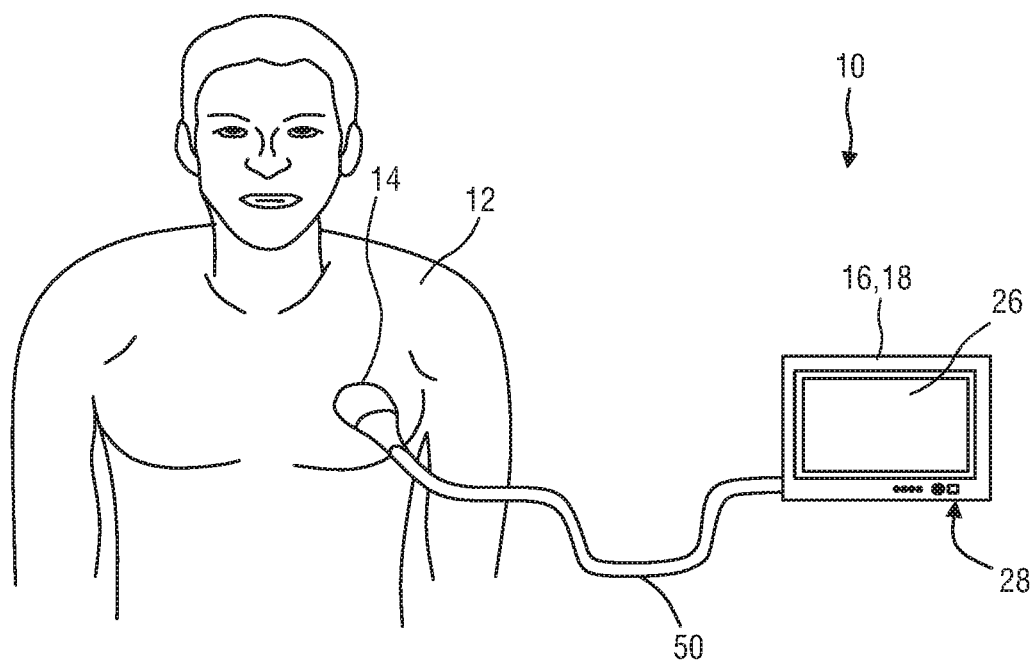
FIG. 1 shows a schematic illustration of an embodiment of an ultrasound imaging system.

FIG. 1 shows an ultrasound imaging system 10. The ultrasound imaging system 10 is used for scanning an area or volume of the body of the patient 12.

For scanning the patient 12, a probe 14 may be provided. In the embodiment shown, the probe 14 is connected to a console device 16, 18. The console device 16, 18 is shown as a mobile console 18 in FIG. 1. The console device 18 is connected to probe 14 via an interface 50 formed in a wired manner in the embodiment 16, shown in FIG. 1. Further, it is contemplated that the console device 16, 18 may be connected to the probe 14 in a wireless manner, for example using UWB transmission technology.

The console device 16, 18 may comprise an input device 28. The input device 28 may have buttons, a keypad and/or a touch screen to provide an input mechanism to a user of the ultrasound imaging system 10. Additionally or alternatively, other mechanisms may be present in the input device 28 to enable a user to control the ultrasound imaging system 10.

Further, the console device 16, 18 comprises a display 26 to display data generated by the ultrasound imaging system 10 to the user. By this, the volume within the patient 12 that is scanned via the probe 14 can be viewed on the console device 16, 18 by the user of the ultrasound imaging system 10.

In particular, the console device 16, 18 may be a mobile console 18. The "mobile console" 18 may be any computational hardware device that may be carried by a user. In particular, the console device 18 may be a cell phone, a PDA (Personal Digital Assistant), a clamshell type personal computer, a tablet type personal computer, a convertible-type personal computer or a hybrid-type personal computer. Further, the console device 18 may also be cart-supported console or non-portable console 16.

Figure 2A:
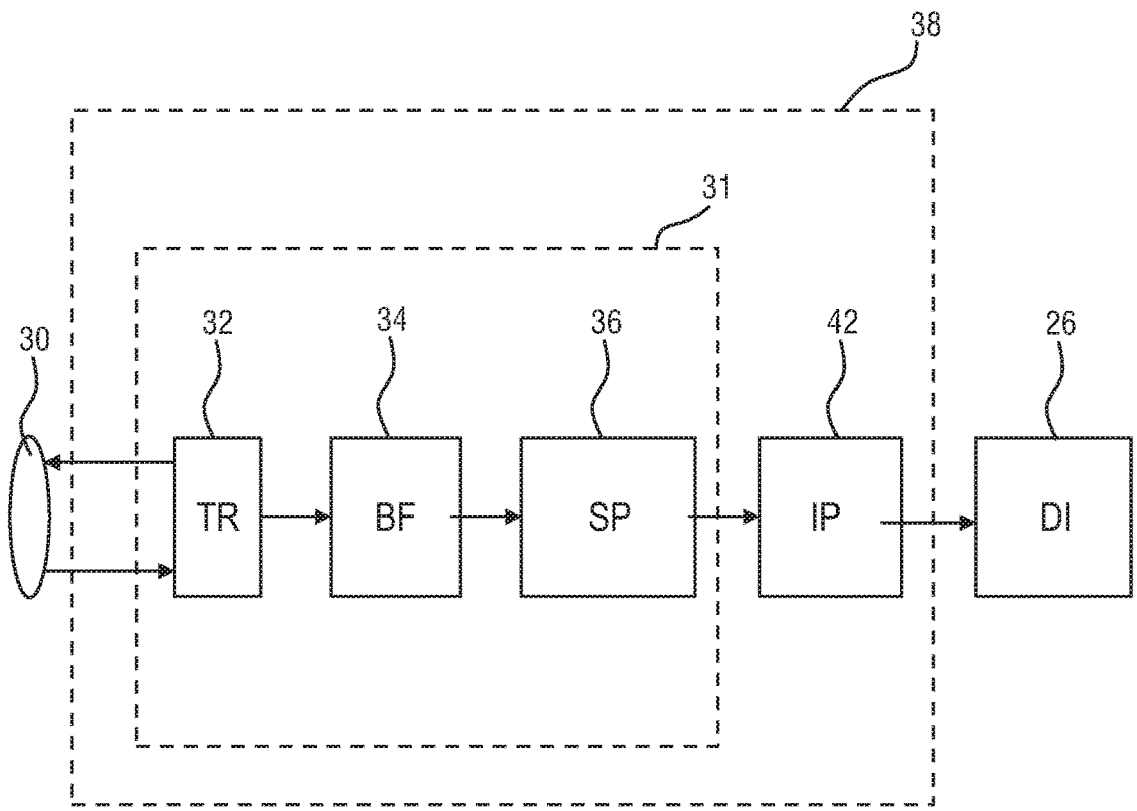
FIG. 2*a* shows a schematic block diagram illustrating the processing of signals and data in an ultrasound imaging system and of an ultrasound image acquisition device.

FIG. 2*a* shows a block diagram illustrating the typical operation of a three-dimensional ultrasound imaging system 10. A transducer array 32 emits ultrasound signals which generate a response from the volume 30 back to the transducer array 32. A beam former 34 explained in more detail below controls the transducer array 32. The beam former 34 provides an image signal to a signal processor 36. The signal processor 36 in turn generates detected acoustic data—the so-called image data—therefrom. An image processor 42 converts the image data into display data to be displayed on the display 26. The image processor 42 may prepare two-dimensional tomographic slices of the volume 30 to be displayed or may convert or render the image data into a three-dimensional image that is displayed on a display 26.

As initially laid out, the acquisition of a three-dimensional image may be accomplished by conducting many two-dimensional scans that slice through the volume 30. Hence, a multitude of two-dimensional images is acquired that lie next to one another with an elevational or rotational displacement. By proper image processing, e.g. shear warp, a three-dimensional image of the volume of interest can be built out of the multitude of two-dimensional images. In case multiple two-dimensional planes are acquired, they may also be displayed side-by-side on the display in a "multi-plane" mode which has significant advantages in particular clinical applications. There are other methods of acquiring voxels, such as by scanning simultaneous quadruplets of receive lines arranged in a rectangular pattern, where the four receive lines utilize simultaneous echoes from a single, centrally placed transmit pulse locus. The quadruplets can be further positioned in any sequence and pattern, including helical.

Further, so called 4D imaging may be enabled, wherein a motorized scanner mechanically sweeps a two-dimensional imaging sensor array in a third dimension to create the three-dimensional scan. Alternatively, so-called "live 3D" imaging may be enabled that refers to electronically scanning in three dimensions using arbitrary scan line planes, but not constrained by the axis of motion of an oscillating motor. A live 3D probe array is typically comprised of elements distributed in more than one dimension, that is, neither in a single flat row of transducer elements nor a single curved row of transducer elements, but on a multi-dimensional surface, such as a rectangle or a portion of a sphere. Accordingly, this matrix array of elements allows more or less arbitrary placement of scan lines, and they are typically organized as described earlier, that is, in distinct scan planes that are assembled as tomographic slices and converted to a three-dimensional volume by the rendering process. The matrix array configuration is generally preferred to the motorized configuration due to the increased freedom to compose arbitrary scan line patterns, the speed of acquisition because the electronic switching of scan line positions is faster than the mechanical movement of the array, the lower power consumption because of no motor, higher reliability because of no moving parts, and potentially lower cost. Thus, an embodiment of this invention would comprise, but not be limited to, a matrix array probe.

An image acquisition hardware assembly 31 may be formed by the transducer array 32, the beam former 34 and the signal processor 36. However, the image processor may also be part of the image acquisition hardware assembly 31. This is depicted by the so-called extended image acquisition hardware assembly 38.

Generally, the beam former 34, the signal processor 36 and/or the image processor may be analogue or digitally implemented hardware devices or software implementations run on a processing unit.

Figure 2B:
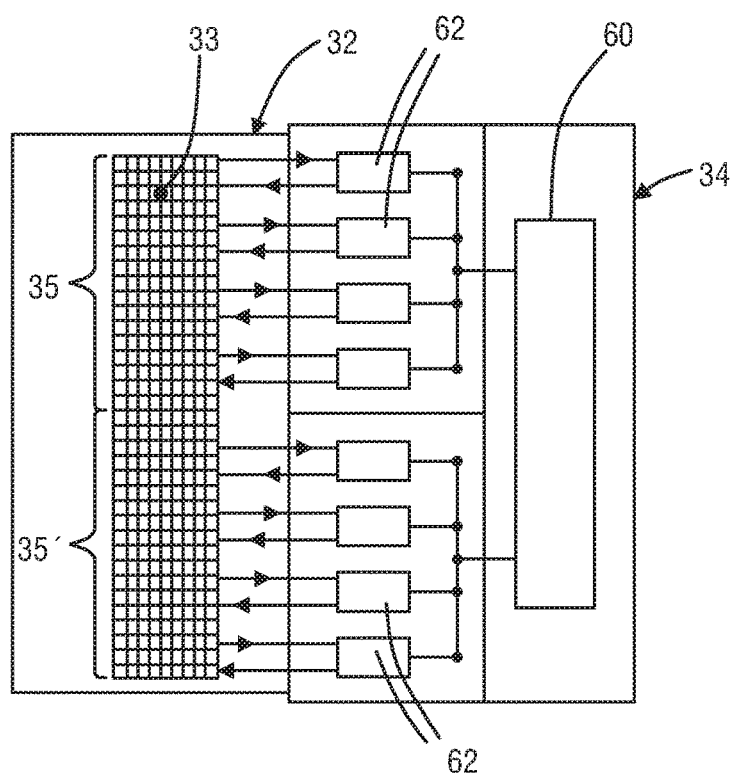
FIG. 2*b* shows an example of a detailed view on a transducer array and a beam former.

FIG. 2b is a schematic detailed view of the transducer array 32 and the beam former 34. The transducer array 32 is formed of a plurality of acoustic elements arranged in a one-dimensional or two-dimensional array. The acoustic elements transmit the ultrasound signals and receive the generated responses. A transducer array 32 may comprise thousands of acoustic elements 33 forming a multitude of sub-arrays 35, 35'. For illustrative purposes, merely two sub-arrays are shown. However, the number of sub-arrays may also be greater than two, e.g. eight. The acoustic elements 33 may, for example, be arranged in a two-dimensional array as a square matrix. However, different shapes such as a rectangular, curved, oval, or circular may also be used, and which is optimal depends mainly on the object being analyzed and the clinical applications.

The transducer array 32 may have of a plurality of micro beam formers 62, which control both transmission and reception of acoustic pulses through the acoustic elements, and combine the acoustic responses generated by the scanned medium in order to form the sub-array summed acoustic signals, which are then transferred from the transducer array 32 through signal lines to the beam former 34. Shown are two groups of each having four micro beam formers 62. However, the number of micro beam formers 62 in each group may also be different from four, e.g. eight or sixteen. In particular, eight groups each having sixteen micro beam formers 62 may be present. Each signal line within a sub-array 35, 35' may emanate from one micro beam former 62 and is joined with the other signals of that sub-array 35, 35' to form a sub-array group output. The sub-array group output is then connected to the main beam former 60 as described below.

There are two main phases of beam forming, namely, transmit and receive. During transmittance, acoustic pulses are generated from acoustic elements of the transducer array 32. During the receive phase, echoes from those pulses in the volume 30 are received by the acoustic elements of the transducer array 32, amplified, and combined. For beam forming in the transmit phase, transmit delay pulsers generate delayed high voltage pulses. The acoustic pulses are transmitted by the acoustic elements. The acoustic pulses are timed relative to each other to generate a focus in the three-dimensional space of the insonified medium. In the receive phase, the acoustic pulses previously transmitted are echoed by structures in the volume 30. Between the time that the acoustic pulses are transmitted and the generated pulse echoes are received by the acoustic elements, so-called T/R (transmit/receive) switches switch to the receive position. Acoustic pulses are received by the acoustic elements from many points on the body, and receive samplers take periodic samples of the resulting acoustic wave to generate analog samples, which are small voltages. The analog samples are then delayed by receive delays. The receive delays may be static delays, meaning they are unchanged during the course of acoustic reception. The receive delays may also be programmable and thereby modified dynamically during the receive phase so as to maintain a constant array focus as the transmitted pulses propagate into the medium and create echoes from successively deeper locations in the medium. The separately delayed received signals are summed together by summers, and after summing, variable gain amplifiers perform time gain compensation. Time variable gain is required because the signals received by the acoustic elements from later times correspond to deeper depths of the body, and are therefore attenuated. The variable gain amplifiers compensate for this attenuation by increasing output. The sub-array summed acoustic signals are transmitted by the signal lines.

Hence, the transducer array 32 provides dynamic or static beamforming to generate a plurality of sub-array summed acoustic signals, which are received by a further static or dynamic beam former in a main beam former 60. The main beam former 60 performs static or dynamic beamforming to generate a set of fully beam formed image signals. Hence, in the current application, the "beam former" 34 denotes the so-called master beam former which is comprised of the micro beam formers 62 and the main beam former 60. Hence, one main beam former 60 sub-groups a multitude of micro beam formers 62. By this, the number of signals from the beam former 34 to the signal processor 36 may be significantly reduced compared to the number of transducer elements.

Examples of such transducer arrays with cascaded beam forming may be the X6-1 or X7-2 type probes commercialized by the applicant.

Figure 3:
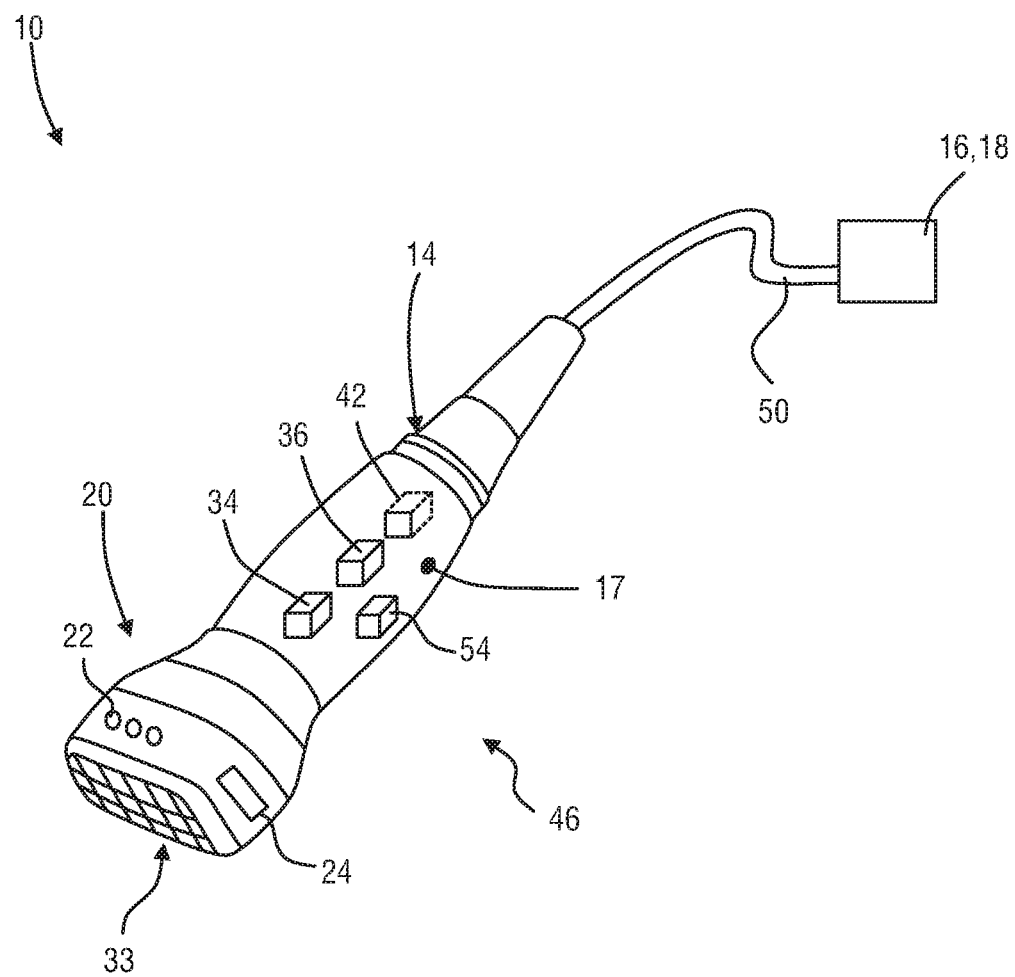
FIG. 3 shows a schematic representation of an ultrasound image acquisition device embodied as a probe.

FIG. 3 shows an embodiment wherein the ultrasound image acquisition device 46 is solely embodied as the probe 14. The probe 14 has a probe housing 17 that includes all necessary ultrasound imaging hardware that is the transducer array 32, the beam former 34, the signal processor 36 and, optionally, the image processor 42. Further, the probe housing 17 may have a further input device 20 having, for example, a button 24 to control the image acquisition. Further, an output device 22 may be provided at the probe, e.g. in the form of a light emitting diode (LED) or a plurality of lights or LEDs 22. The probe 14 is connected via an interface 50 to the console device 16, 18. The embodiment shown in FIG. 3, the interface 50 is a wired connection. Mobile live three-dimensional ultrasound imaging is thus enabled. This provides a user with flexibility in customizing and optimizing individual use models of the console device 16, 18.

Figure 4:
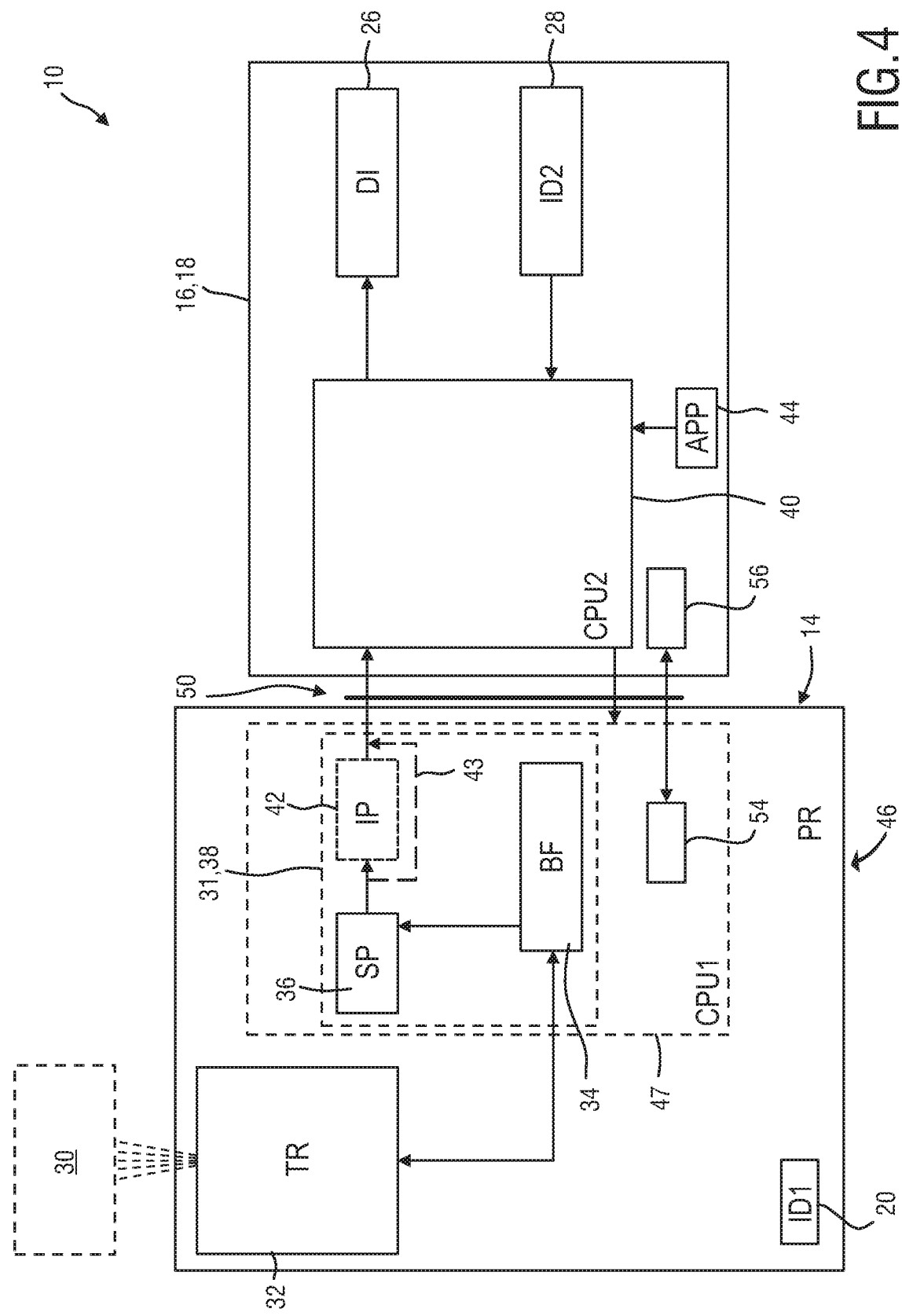
FIG. 4 shows a schematic block diagram of an embodiment of an ultrasound imaging system.

FIG. 4 shows a schematic block diagram as an example for the various components of the ultrasound imaging system 10 and their location and interaction within the whole ultrasound imaging system 10.

As already explained above, the ultrasound imaging system 10 is used for scanning a volume of a patient 12. The volume is schematically shown in dashed lines and designated with reference numeral 30. The area is examined via the probe 14 carrying a transducer array 32. The transducer array 32 may be of any known type. Hence, the transducer array 32 may be a one-dimensional transducer array or a two-dimensional transducer array that may be mechanically or electronically scanned. The transducer array 32 converts the ultrasound signals into electronic signals and vice versa.

To command the transducer array 32, the beam former 34 is present that is used to control the electronic and/or mechanical scanning of the transducer array and, if possible, the number, density and position of scan lines along which the area 30 is scanned. Further, the signal processor 36 may be provided that receives the ultrasound image signal of the beam former and provides image data. The beam former 34 and the signal processor 36 together may form an image acquisition hardware assembly 31 of an ultrasound image acquisition device 46, for example a probe 14.

The image processor 42 receives image data from the signal processor 36 and provides display data to the display 26. The beam former 34, the signal processor 36 and the image processor 42 may be run by the central processing unit 47. In an embodiment, the signal processor 36 and/or the image processor 42 may be of a software-implemented type and run on the central processing unit 47 of the probe 14. However, it may also be the case that at least one or two of the group of the signal processor 36, the beam former 34 and the image processor 42 is/are of a hardware-implemented type. The location of the respective circuitry is preferably as shown in FIG. 4.

The probe 14 comprises, therefore, all necessary ultrasound acquisition hardware in the form of an ultrasound image acquisition hardware assembly 31. The image processor 42 is merely optional inside the probe 14. It may alternatively be provided by the console device and its central processing unit 40. Hence, the image processor 42 in FIG. 4 is merely depicted in dashed lines. If not present, the signal processor 36 forwards this data directly to the central processing unit 40 of the console device 18 as indicated via the dashed line 43. Further, instead of a software implementation into this central processing unit 40 of the console device 18, the image processor 42 may also be hardware implemented in the console device 18. The software implemented image processor 42 may also be part of an application 44 run on the central processing unit 40 of the console device to provide display data for display on the display device 26.

However, an extended image acquisition hardware assembly 38 may be formed in the probe 14 if the image processor 42 is also present in the probe. The probe 14 may comprise a central processing unit 47 controlling one or more operations of the probe 14. Hence, the signal processor 36 and/or the image processor 42 (if present) may be software implemented and run on the central processing unit 47 of the probe 14. However, the signal processor 36 and/or the image processor 42 may also be hardware implemented in the probe 14 for efficiency or as an application specific integrated circuit (ASIC). The first input device 20 of the probe 14 may, in any embodiment, be used to provide simple control of the image acquisition process, like a button to start and stop the image acquisition process.

Further, the ultrasound image acquisition device 46 comprises a recognition device 54 for recognizing an operating mode of the ultrasound image acquisition device, wherein the recognition device 54 is configured to recognize the operating mode depending on a type of the console device 16, 18 and/or an applicable communication standard of the interface 50. As will be explained in further detail below, this enables the ultrasound image acquisition device to switch the image acquisition hardware assembly 31 and/or the image processor 42 into at least two different operating states. By this, in particular power consumption and the type of image acquisition, e.g. two-dimensional only or three-dimensional, of the ultrasound image acquisition device 46 may be altered. This enables usage of the ultrasound image acquisition device 10 with both mobile consoles 18 and non-portable or cart-based consoles 16.

The console device 16, 18 may include a recognition partner element 56 that may identify a type of the console device 16, 18 to the recognition device 54.

As is apparent from FIG. 4, the console device 18 does not need any specific ultrasound image acquisition hardware. An input device as the input device 28, a display as the display 26 and a central processing unit as the central processing unit 40 are frequently present on any console device that is commercially available off the shelf. A specific software or app 44 may then be downloadable or may be stored on the console device 18 and run on the central processing unit 40 to view the display data with the rendered images of the volume 30. The operating system stored on the console device 18 may for example be a Windows operating system, an Android operating system or an iPhone iOS operating system.

In an embodiment, the transducer 32 is a two-dimensional phased-array matrix-type transducer array which is electronically scanned and micro beam formed to a plurality of channel signals which are further beam formed and demodulated inside the probe 14. Then, as the interface 50, an interface working with USB 2.0 and/or 3.0 standards may be used to connect the probe 14 to the console device 18.

Figure 5:
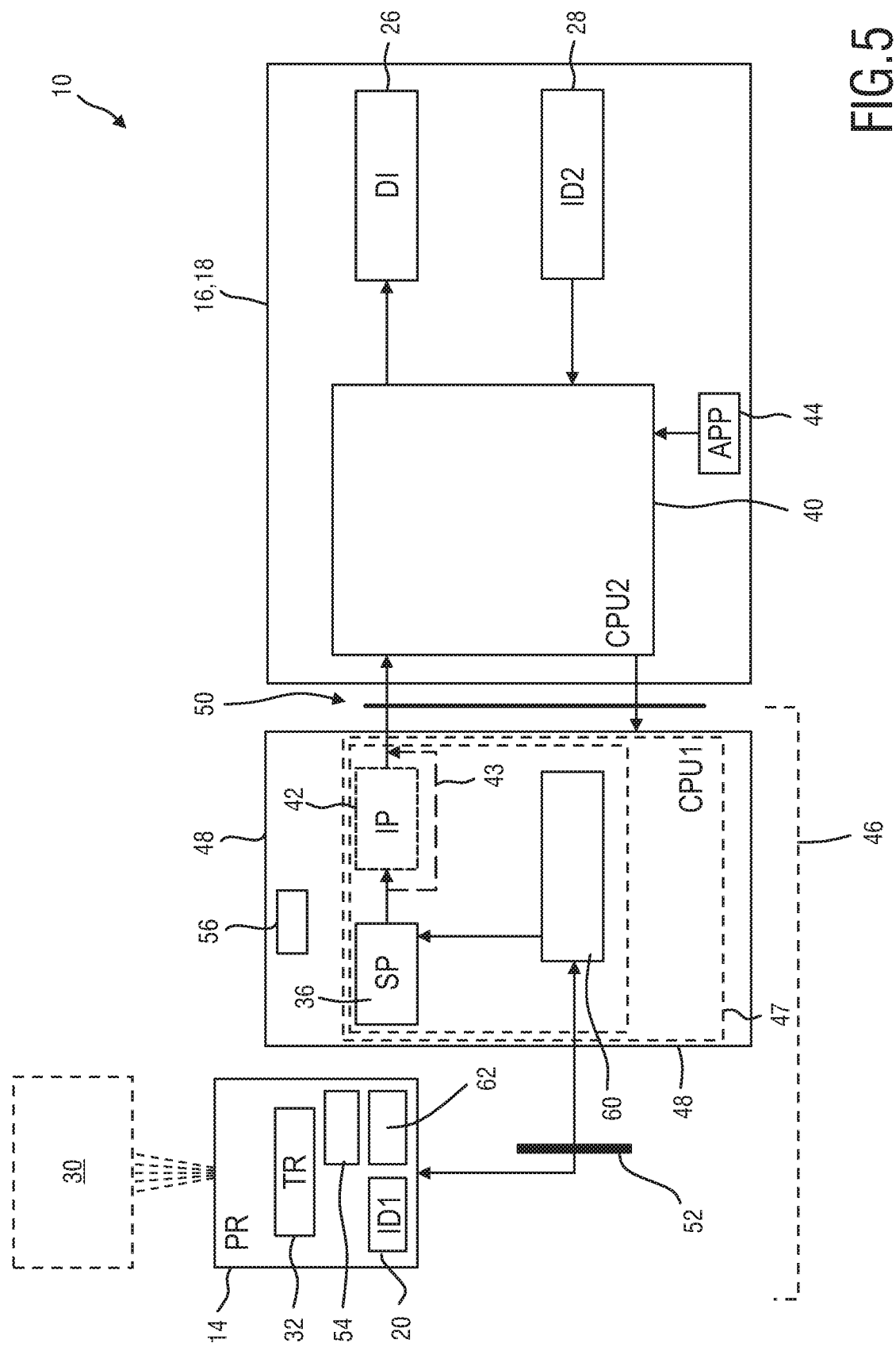
FIG. 5 shows a block diagram of a further embodiment of an ultrasound imaging system.

FIG. 5 shows a further embodiment of an ultrasound imaging system 10. Like elements are denoted with like reference numerals and will not be explained again. This embodiment also provides for the advantage that the console device 18 does not need to comprise any ultrasound specific hardware. Again, a display 26, an input device 28 and a central processing unit 40 in which an application 44 is run to display the display data on the display device 26 is sufficient. Also, the interface 50 may be as previously explained, it may be cable connected.

However, in this embodiment, the image acquisition device 46 is not solely implemented in the probe 14. Instead, the probe carries the transducer array 32, the micro beam formers 62 and, optionally, a first input device 20. Further, there is provided an intermediate connection device 48 as part of the image acquisition device 46 that is connected via an intermediate interface 52 with the probe 14. In particular, the intermediate connection device 48 can be portable. The intermediate interface 52 may be a cable connection. However, in this case, preferably the interface 50 connecting the intermediate connection device with the console device 16, 18 is implemented wirelessly. For example, if the interface 50 is a wireless interface, the UWB technology may be used. In case the intermediate interface 52 is cable-connected, the interface 52 may also include a power line to power the probe 14 and the intermediate connection device 48 may include a battery for powering both the intermediate connection device 48 and the transducer array 32. In case the interface 50 is wireless, the intermediate connection device 48 may be powered by a battery. In that case the same battery may also provide power to both the intermediate connection device 48 and probe 14. However, the intermediate connection device 48 may also be provided with a wired power connection.

Figure 6:
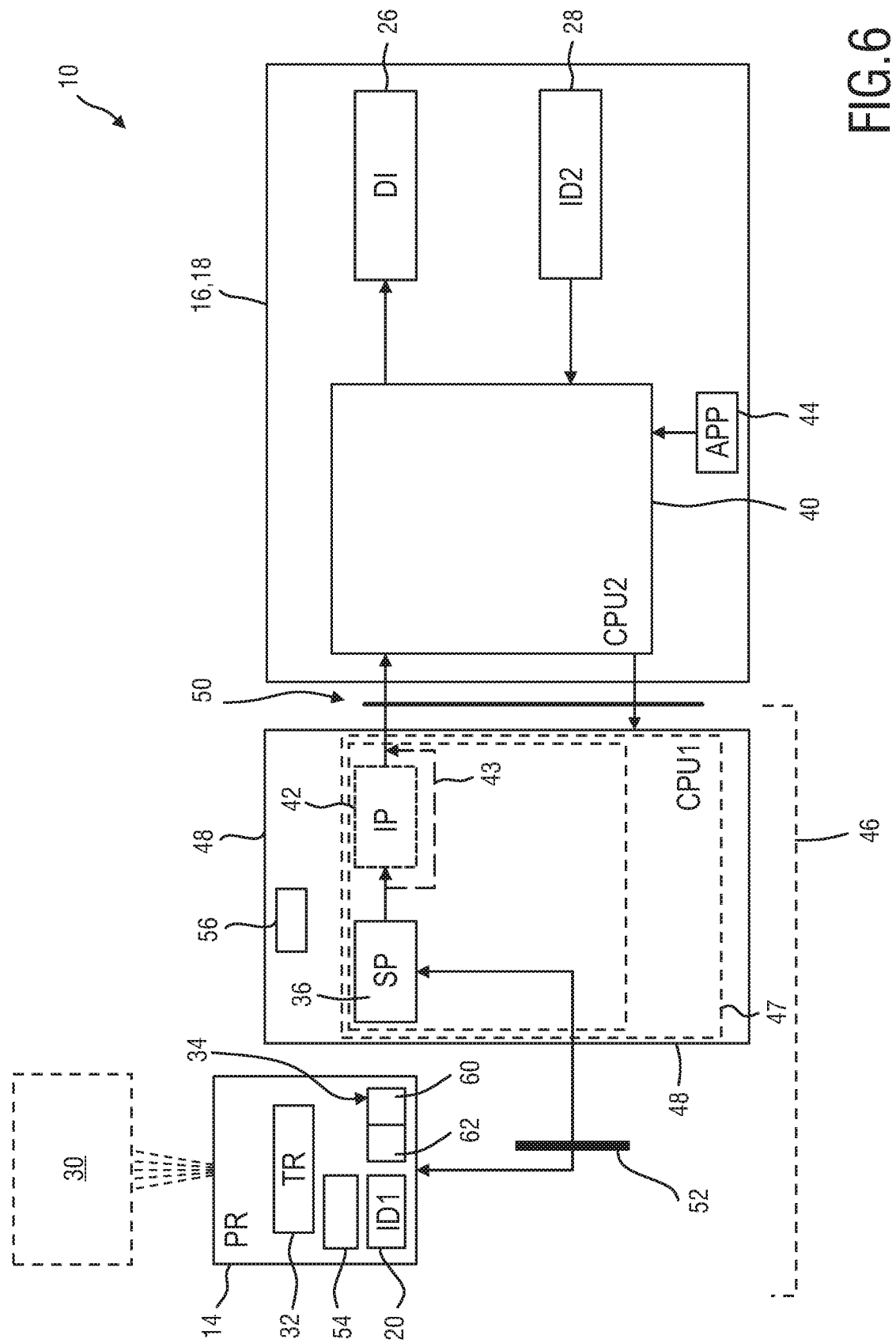
FIG. 6 shows a block diagram of another embodiment of an ultrasound imaging system.

FIG. 6 shows a further embodiment similar to that of FIG. 5. Like elements are designated with like reference numerals and will not be explained again. In this embodiment, the probe 14 also comprises the main beam former 60 and, hence, the whole beam former 34. By this, the size of the probe 14 may be reduced, also. The signal processor 36 is located in the intermediate connection device 48. The image processor 42 may still be located in the intermediate connection device 48. Alternatively, it may be located in the console device 18.

Figure 7:
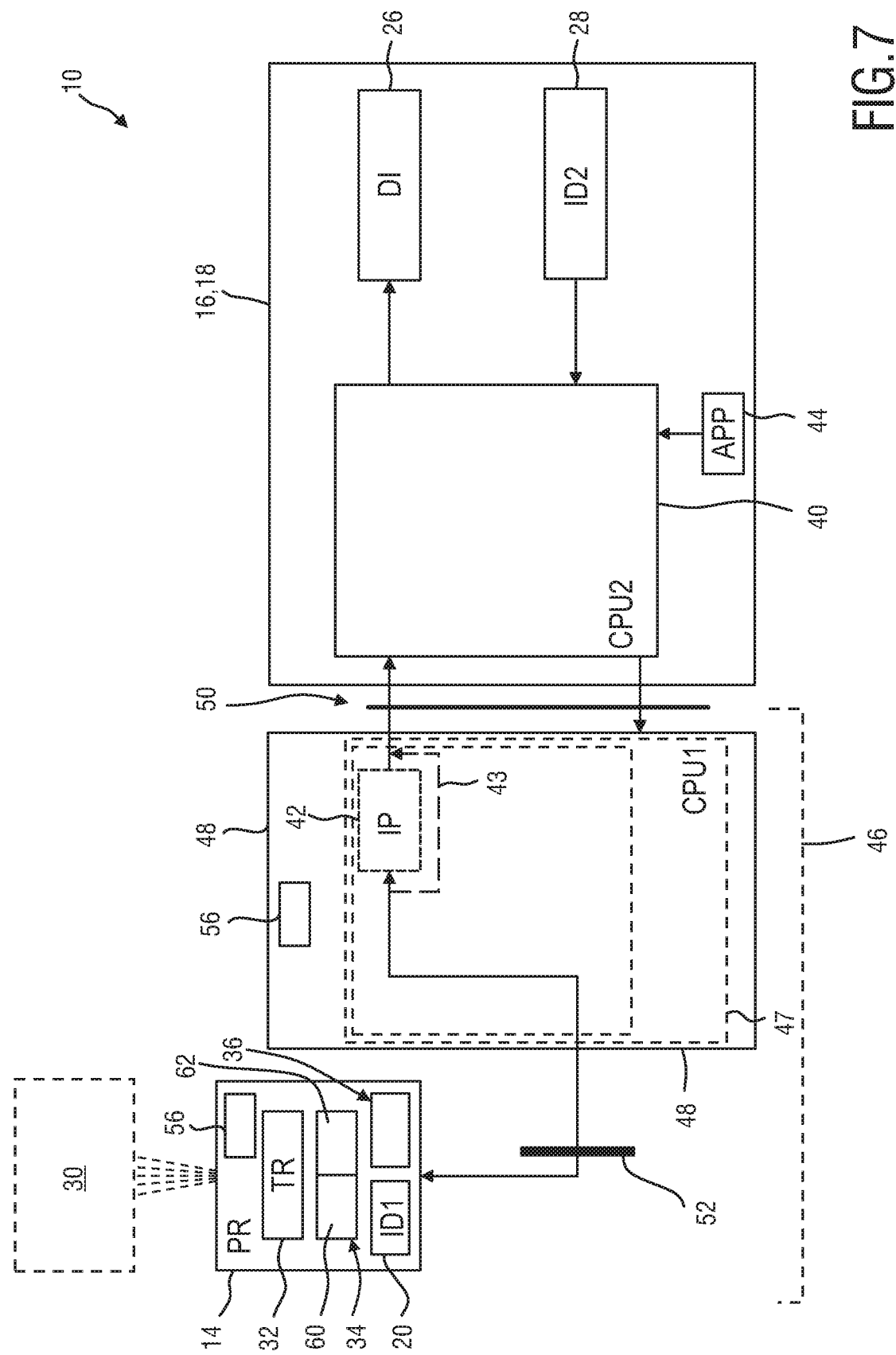
FIG. 7 shows a block diagram of yet another embodiment of an ultrasound imaging system.

FIG. 7 shows a further embodiment similar to that of FIG. 6. Like elements are designated with like reference numerals and will not be explained again. In this embodiment, the probe 14 also comprises the signal processor 36. By this, the size of the probe may be reduced, also. The image processor 42 producing some of the heat dissipated by its circuitry may still be located in the intermediate connection device 48.

Figure 8:
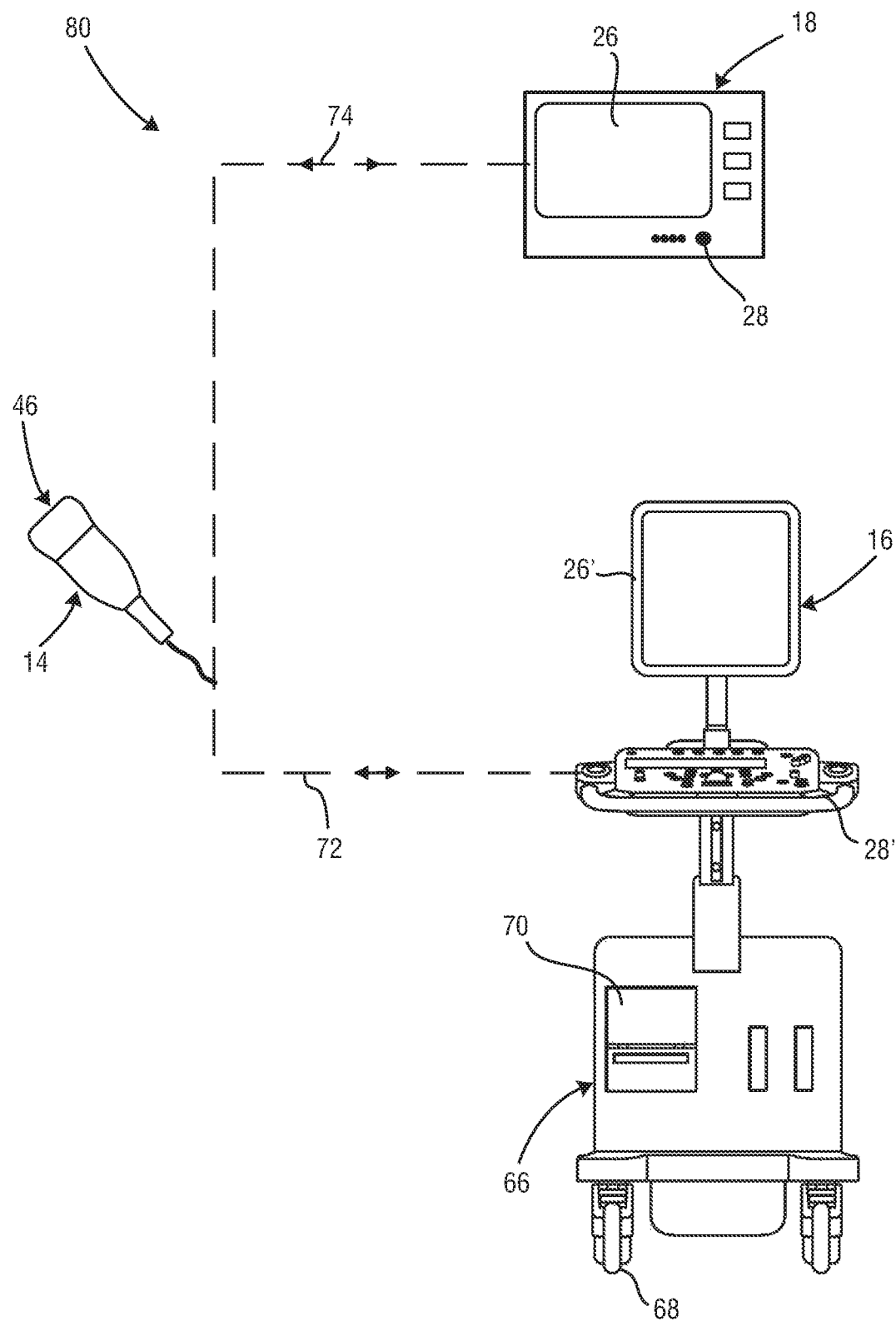
FIG. 8 shows a schematic illustration of an embodiment of an ultrasound image acquisition kit.

FIG. 8 shows a general overview of an embodiment of a kit for ultrasound imaging. As already explained in the above, the ultrasound image acquisition device 46 may be, as in the depicted example, a probe 14 that may be either connected to a mobile console 18 or a cart-based console 16. Hence, the probe 14 together with the mobile console 18 may form an ultrasound imaging system 10 according to an embodiment. To the alternative, the probe 14 connected to the cart-based console 16 may also form an ultrasound imaging system 10. A cable connection to the mobile console is depicted with a dashed line designated by reference numeral 74. The cabled connection to the cart-based console 16 is indicated via a dashed line designated by reference numeral 72. Altogether, the cart-based console 16 and the mobile console 18 together with the probe 14 may form an ultrasound image acquisition kit 80 that enables a user to selectively attach a single probe 14 to different console devices 16, 18.

In particular, the cart-based console 16 also comprises a display 26' and an input device 28'. Further, the display 26' and the input device 28' are supported by the cart 66 that may be based on wheels 68. In particular, the cart-based console 60 may comprise further image acquisition and processing hardware assembly 70. The further image acquisition and processing hardware assembly 70 may comprise a further signal processor, beam former and/or image processor. This further image acquisition and processing hardware assembly may support and enhance the image acquisition hardware assembly 31 (or extended assembly 38) already provided in the probe. Hence, when connected to the cart-based or non-portable console 16, sophisticated ultrasound imaging techniques can be provided.

In particular, two different operating states for the image acquisition hardware assembly 31 of the probe 14 may be provided. For example, the probe 14 may be configured such that it may use either an USB 3.0 or 2.0 standard. When connected to the mobile console 18, the communication standard USB 2.0 will be automatically be recognized via a handshake procedure of the USB protocol and, hence, the recognition device 54 automatically sets a first operation mode and a first operating state of the image acquisition hardware assembly 31 that uses less power and provides "only" two-dimensional or multi-planar image acquisition. Further, when the probe is connected to the non-portable console 16, in a handshake procedure of the communication standard, an USB 3.0 protocol is established and hence, the recognition device 54 in the probe 14 recognizes that the console device 16 is a non-portable or cart-based console. Hence, a second operating mode and a communication standard enabling higher data transfer rates is recognized. The ultrasound image acquisition hardware assembly 31 will be set to a second operating state that enables more sophisticated ultrasound imaging, for example three-dimensional ultrasound imaging. Although such a second operating state may consume more power, and has a higher data transfer rate, this is enabled via the USB 3.0 standard and a power line or conductor from the non-portable console 16 to the probe 14.

Figure 9:
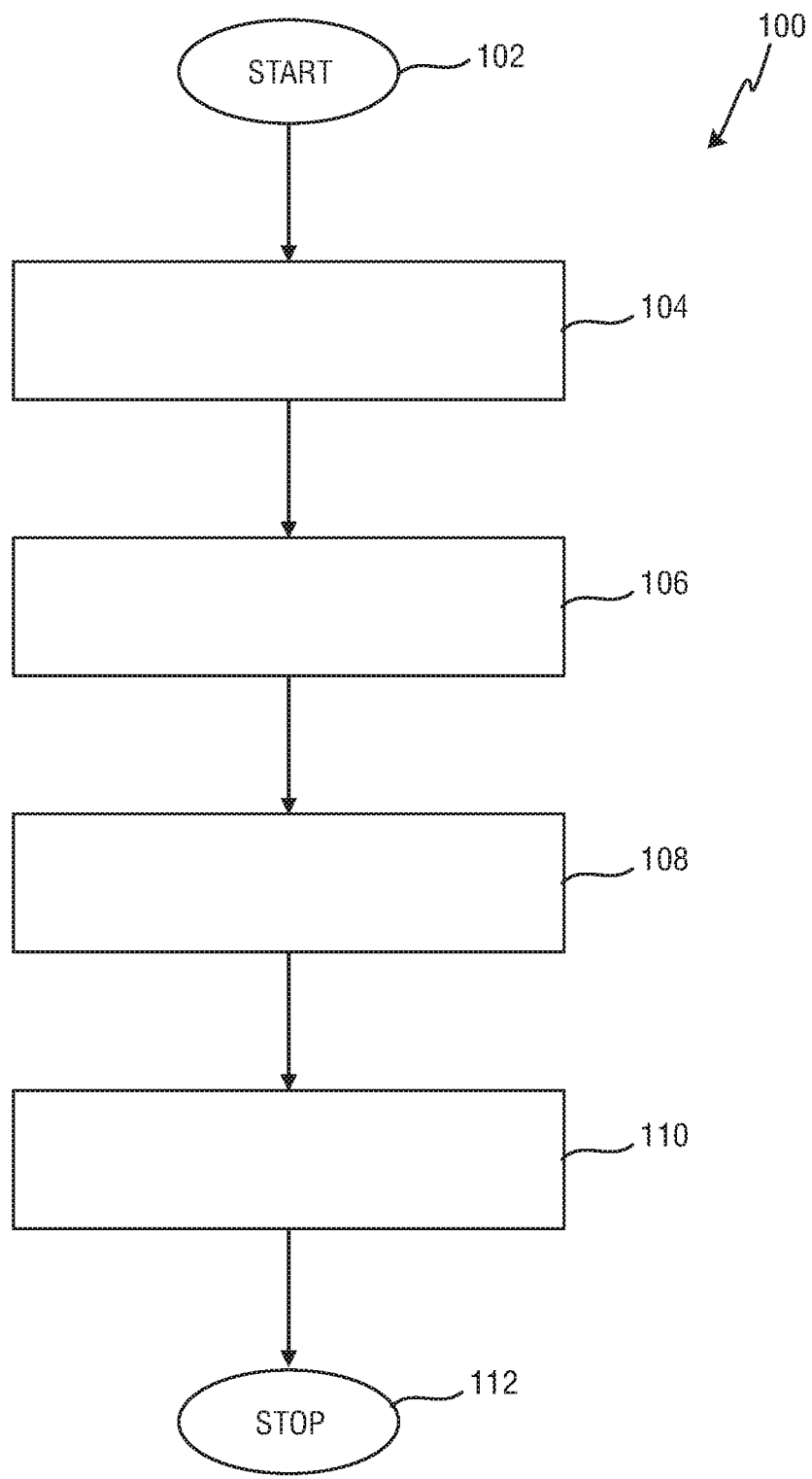
FIG. 9 shows a schematic flow diagram illustrating an embodiment of a method.

FIG. 9 shows a schematic flow diagram of a method 100 according to the invention.

The method starts in a starting step 102. First, in step 104 an ultrasound image acquisition device 10 as explained above is provided. In particular, the ultrasound image acquisition device 10 comprises a transducer array 32 configured to provide an ultrasound receive signal, an image acquisition hardware assembly 31 having a beam former 34 configured to control the transducer array 32, and further configured to receive the ultrasound receive signal and to provide an image signal, and a signal processor 36 configured to receive the image signal and to provide image data, an interface 50 for connecting the ultrasound image acquisition device with a console device 16, 18, and a recognition device 54 for recognizing an operating mode of the ultrasound image acquisition device, wherein the recognition device is further configured to recognize the operating mode depending on a type of the console device and/or an applicable communication standard of the interface.

Then in a step 106, the ultrasound image acquisition device 46 is connected to a console device that may be either a mobile console 16 or a cart-based console 18.

Then, as explained above, in a step 108, the recognition device 54 recognizes an operating mode depending on a type of the console device 16, 18 via the recognition device 54 of the ultrasound image acquisition device 10. An operating state of the image acquisition hardware assembly is set. Hence, the transducer array 32 and/or the image acquisition hardware assembly 31 are switched between at least two operating states based on the recognized operating mode.

Now, the specifying method ends in a step 112. Then, ultrasound image acquisition can be conducted in the specified operating state. In case the probe 14 is disconnected from a console device 16, 18 and reconnected to a console device 16, 18, the method starts over and newly recognizes and switches a corresponding operating mode.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. An ultrasound imaging system, comprising:
    an image acquisition device comprising a first image acquisition hardware assembly, the first image acquisition hardware assembly including a transducer array configured to transmit ultrasound pulses and to receive ultrasound receive signals, a first beamformer, and a first signal processor configured to generate image data based at least in part on the ultrasound receive signals;
    a console device selected from a first type of console device comprising a mobile device and a second type of console device comprising a cart-supported console, wherein the first type of console device is associated with a first Universal Serial Bus (USB) communication standard and the second type of console device is associated with a second USB communication standard, and wherein the second type of console device includes a second image acquisition hardware assembly comprising a second beamformer and a second signal processor; and
    a communication interface coupling the image acquisition device to the console device, wherein the communication interface is configured to use a central processing unit (CPU) of the image acquisition device to recognize the type of the console device, wherein the communication interface is configured, in response to a determination that the console device is of the second type, to use the CPU to automatically switch an operating state of the image acquisition device from a first operating state in which the image data is generated for display by the console device at a first frame rate to a second operating state in which the image data is generated for the display by the console device at a second frame rate higher than the first frame rate, wherein the second image acquisition hardware assembly supports the first image acquisition hardware assembly in the second operating state, wherein the communication interface is configured to use the CPU to determine the type of the console device based on a determination of whether the console device is associated with the first USB communication standard or the second USB communication standard, and wherein the second operating state is associated with an increased transfer rate or increased power provided by the second USB communication standard.

2. The ultrasound system of claim 1, wherein the second operating state enables a volume ultrasound image acquisition and the first operating state enables a planar ultrasound image acquisition but not volume ultrasound image acquisition.

3. The ultrasound system of claim 1, wherein the image acquisition device further comprises a portable probe having a probe housing, wherein the transducer array is located within the probe housing.

4. The ultrasound system of claim 1, wherein the image acquisition device further comprises an image processor configured to receive the image data and to provide the image data for the display.

5. The ultrasound system of claim 1, wherein the communication interface comprises a cable-connected interface.

6. The ultrasound system of claim 5, wherein the communication interface further comprises a power line powering the ultrasound image acquisition device.

7. The ultrasound system of claim 1, wherein the console device comprises a display unit and an input device.

8. The ultrasound system of claim 1, wherein the determination of whether the console device is associated with the first USB communication standard or the second USB communication standard is based on a handshake procedure responsive to a connection between the image acquisition device and the console device.

* * * * *